US012622774B2

(12) United States Patent
Strotman et al.

(10) Patent No.: US 12,622,774 B2
(45) Date of Patent: May 12, 2026

(54) METHOD OF WHITENING TEETH

(71) Applicant: Colgate-Palmolive Company, New York, NY (US)

(72) Inventors: Hallena Strotman, Somerset, NJ (US); Leighton Davies-Smith, Lebanon, NJ (US)

(73) Assignee: Colgate-Palmolive Company, New York, NY (US)

( * ) Notice: Subject to any disclaimer, the term of this patent is extended or adjusted under 35 U.S.C. 154(b) by 721 days.

(21) Appl. No.: 17/633,270

(22) PCT Filed: Sep. 3, 2020

(86) PCT No.: PCT/US2020/070487
§ 371 (c)(1),
(2) Date: Feb. 7, 2022

(87) PCT Pub. No.: WO2021/056007
PCT Pub. Date: Mar. 25, 2021

(65) Prior Publication Data
US 2022/0338968 A1       Oct. 27, 2022

Related U.S. Application Data

(60) Provisional application No. 62/902,800, filed on Sep. 19, 2019.

(51) Int. Cl.
| | |
|---|---|
| *A61C 19/06* | (2006.01) |
| *A61K 8/22* | (2006.01) |
| *A61N 5/06* | (2006.01) |

(52) U.S. Cl.
CPC .............. *A61C 19/066* (2013.01); *A61K 8/22* (2013.01); *A61N 2005/0606* (2013.01)

(58) Field of Classification Search
CPC ..... A61C 19/066; A61C 19/063; A61C 19/06; A61N 2005/0606; A61N 1/0548; A61N 1/325
See application file for complete search history.

(56) References Cited

U.S. PATENT DOCUMENTS

| | | | |
|---|---|---|---|
| 5,785,527 | A | 7/1998 | Jensen et al. |
| 6,254,388 | B1 | 7/2001 | Yarborough |
| | | (Continued) | |

FOREIGN PATENT DOCUMENTS

| | | |
|---|---|---|
| WO | 1998/30494 | 7/1998 |
| WO | 2007/005028 | 1/2007 |
| | (Continued) | |

OTHER PUBLICATIONS

Colgate website, ShopSmiles by Colgate, Colgate Optic White Advanced LED Whitening, LED Teeth Whitening Device & 10-Day Treatment, https://shop.colgate.com/products/teeth-whitening-led-device-kit [online] retrieved Feb. 7, 2022, pp. 1-2.
(Continued)

*Primary Examiner* — Heidi M Eide
*Assistant Examiner* — Shannel Nicole Belk

(57) ABSTRACT
A method of whitening teeth that decreases the amount of time that the whitening composition is in contact with the teeth. Specifically, by pretreating the whitening composition with light before contacting the teeth with the whitening composition, the amount of time that the whitening composition needs to be in contact with the teeth can be reduced. In one aspect, the method may include dispensing a tooth whitening composition from a reservoir device into a channel of a mouth tray; activating an electromagnetic radiation source to emit light onto the tooth whitening composition in the channel of the mouth tray for a first period of time to pretreat the tooth whitening composition; and inserting the mouth tray into the oral cavity of the user so that the user's
(Continued)

teeth are in contact with the tooth whitening composition in the channel for a second period of time to whiten the teeth.

20 Claims, 6 Drawing Sheets

(56) References Cited

U.S. PATENT DOCUMENTS

| | | | |
|---|---|---|---|
| 7,645,137 B2 * | 1/2010 | Wasyluch | A61Q 11/00 |
| | | | 433/29 |
| 8,075,875 B2 | 12/2011 | Piergallini et al. | |
| 8,172,570 B2 | 5/2012 | Baughman | |
| 8,795,636 B2 | 8/2014 | Jablow | |
| 9,492,257 B2 | 11/2016 | Jablow et al. | |
| 10,285,790 B2 | 5/2019 | Wasylucha | |
| 10,369,375 B2 | 8/2019 | Demarest et al. | |
| 2004/0110111 A1 * | 6/2004 | Wasylucha | A61C 19/063 |
| | | | 433/29 |
| 2006/0019214 A1 * | 1/2006 | Lawrence | A61C 19/066 |
| | | | 433/29 |
| 2007/0015112 A1 | 1/2007 | Hochman et al. | |
| 2008/0118446 A1 | 5/2008 | Jablow | |
| 2008/0131843 A1 | 6/2008 | Montgomery et al. | |
| 2008/0260660 A1 | 10/2008 | Engelbrecht et al. | |
| 2011/0076636 A1 * | 3/2011 | Wolff | A61C 19/063 |
| | | | 433/29 |
| 2011/0117515 A1 | 5/2011 | Jablow | |
| 2013/0045457 A1 | 2/2013 | Chetiar et al. | |
| 2015/0072302 A1 | 3/2015 | Jablow | |
| 2017/0173353 A1 * | 6/2017 | Demarest | A61C 19/066 |
| 2017/0173357 A1 | 6/2017 | Demarest et al. | |
| 2020/0230432 A1 * | 7/2020 | Jablow | A61C 19/066 |
| 2021/0008384 A1 * | 1/2021 | Lee | A61C 17/06 |

FOREIGN PATENT DOCUMENTS

| | | |
|---|---|---|
| WO | 2010/040980 | 4/2010 |
| WO | 2020/076471 | 4/2020 |
| WO | 2021/056007 | 3/2021 |

OTHER PUBLICATIONS

International Search Report and the Written Opinion of the International Searching Authority issued in International Application PCT/US2020/070487 mailed Nov. 25, 2020, pp. 1-13.

Smile website, iSmile Teeth Whitening Kit, https://shopismile.com/collections/frontpage/products/deluxe-home-teeth-whitening-system?gclid=CjwKCAjwtuLrBRAIEiwAPVcZBkxLYel_etdfljlpg80sXdnHKL2XGyu-w-r7uZNnGYFXbOMhH9FbFhoCJjYQAvD_BWE [online] retrieved Feb. 7, 2022, pp. 1-9.

* cited by examiner

|  | Treatment #1 | Treatment #2 | Treatment #3 | Treatment #5 | Treatment #8 | Treatment #10 |
|---|---|---|---|---|---|---|
| 9% HP Gel + Light | -9.13 | -16.32 | -19.16 | -21.27 | -23.24 | -23.69 |
| Activated 9% HP Gel + Light | -6.85 | -19.34 | -21.54 | -22.73 | -22.87 | -24.78 |

|  | Treatment #1 | Treatment #2 | Treatment #3 | Treatment #5 | Treatment #8 | Treatment #10 |
|---|---|---|---|---|---|---|
| 0.1% HP Gel + Light | -4.17 | -6.65 | -7.75 | -9.57 | -12.12 | -12.80 |
| Activated 0.1% HP Gel + Light | -1.91 | -2.98 | -3.43 | -5.37 | -7.64 | -8.58 |

METHOD OF WHITENING TEETH

BACKGROUND

Many individuals are dissatisfied with their current tooth color. There are a range of tooth whitening products on the market including toothpastes, gels, trays, strips, and professional treatments. The color of human teeth comes from the combined color of the enamel and dentin. Enamel is a semi-transparent material that covers human teeth and thins over the course of time. The natural color of teeth becomes more yellow over time due to this thinning along with the accumulation of stains. These stains come from many sources such as medications, diet, and lifestyle choices. There are two different types of tooth stains that occur, extrinsic and intrinsic stains. Extrinsic stains are usually removed through the mechanical action of the abrasive system in a toothpaste in combination with the brushing action of the toothbrush. Intrinsic stains are accessible through bleaching agents such as hydrogen peroxide that can penetrate the surface of the enamel. The ability of bleaching agents to penetrate the surface of the tooth depends on many factors, including bleaching agent molecular size and concentration along with contact time with the surface. Longer contact time between the bleaching agents and the teeth is undesirable because: (1) it takes up too much of a user's time; and (2) there is a perception that longer contact time can cause greater sensitivity. Thus, a need exists for a tooth whitening method that reduces the amount of time that the bleaching agent is in contact with the teeth.

BRIEF SUMMARY

The present invention is directed to a method of whitening teeth that decreases the amount of time that the whitening composition is in contact with the teeth without diminishing the whitening result. Specifically, it has been found that by pretreating the whitening composition with light before contacting the teeth with the whitening composition, the amount of time that the whitening composition needs to be in contact with the teeth to achieve the same or better whitening effect can be reduced.

In one aspect, the invention may be a method of whitening teeth comprising: dispensing a tooth whitening composition from a reservoir device into a channel of a mouth tray; prior to placing the mouth tray into a mouth of a user, activating an electromagnetic radiation (i.e., illumination) source to emit light onto the tooth whitening composition in the channel of the mouth tray for a first period of time to pretreat the tooth whitening composition; after expiration of the first period of time, inserting the mouth tray into the mouth of the user so that the user's teeth are in contact with the tooth whitening composition in the channel for a second period of time to whiten the teeth; and after expiration of the second period of time, removing the mouth tray from the mouth of the user and deactivating the electromagnetic radiation source.

In another aspect, the invention may be a method of whitening teeth comprising: dispensing a tooth whitening composition into a channel of a mouth tray; emitting light onto the tooth whitening composition in the channel of the mouth tray for a first period of time; after expiration of the first period of time, inserting the mouth tray into a mouth of a user so that the user's teeth are in contact with the tooth whitening composition in the channel for a second period of time; and wherein a sum of the first and second periods of time equals a total treatment time, and wherein the first period of time is at least 20% of the total treatment time.

In yet another aspect, the invention may be a method of whitening teeth comprising: dispensing a tooth whitening composition into a channel of a mouth tray; emitting light onto the tooth whitening composition in the channel of the mouth tray for a non-contact treatment time; and inserting the mouth tray into a mouth of a user so that the user's teeth are in contact with the tooth whitening composition in the channel of the mouth tray for a contact treatment time; and wherein a ratio of the contact treatment time to the non-contact treatment time is approximately 1:1.

In a further aspect, the invention may be a method of whitening teeth comprising: a pretreatment step comprising emitting light onto a tooth whitening composition in a channel of a mouth tray for a first period of time; a treatment step comprising inserting the mouth tray into a mouth of the user so that the user's teeth are in contact with the tooth whitening composition in the channel of the mouth tray for a second period of time while the light continues to be emitted onto the tooth whitening composition in the channel of the mouth tray; wherein a sum of the first and second periods of time equals a treatment duration; and wherein the treatment duration is equal to a standard treatment time of a standard whitening method that comprises the treatment step and omits the pretreatment step.

In a still further aspect, the invention may be an oral treatment apparatus comprising: a mouth tray comprising a tooth receiving channel for receiving a user's teeth during a tooth whitening procedure and an electromagnetic radiation source configured to emit electromagnetic radiation into the tooth receiving channel; a power source; a processor; a timer device operably coupled to the processor; a first indicator operably coupled to the processor a second indicator operably coupled to the processor; wherein the processor is configured to: start the timer device upon activation of the electromagnetic radiation source; activate the first indicator upon expiration of a first period of time to instruct the user to insert the mouth tray into the oral cavity; and activate the second indicator upon expiration of a second period of time to instruct the user to remove the mouth tray from the oral cavity.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
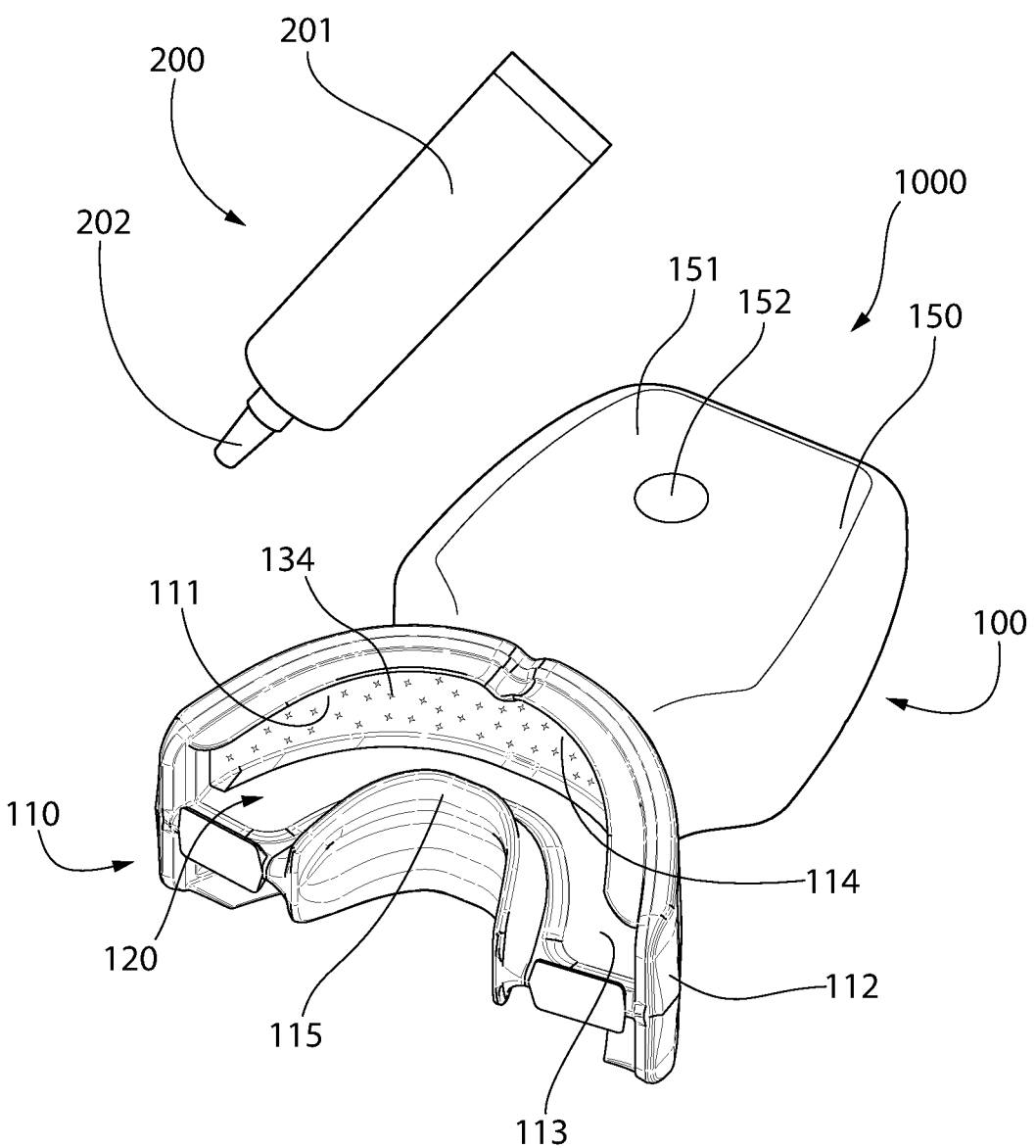
FIG. 1 is a perspective view of a mouth tray and a reservoir device prior to dispensing a tooth whitening composition from the reservoir device into the mouth tray.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

The present invention is directed to a method for whitening teeth. In typical tray-based whitening systems and methods, a tooth whitening composition is dispensed into the tray and then the tray is placed inside of the user's oral cavity with the user's teeth in contact with the tooth whitening composition in the tray. In some systems, a light may then be activated to accelerate the whitening process. The tray is kept in the user's oral cavity for a predetermined period of time, for example around ten minutes, and then the tray is removed from the mouth. This treatment is repeated as many times as desired by the user over a span of several days or weeks to achieve the desired whitening effect. The present invention is directed to a method that reduces the amount of time that the tooth whitening composition is in contact with the teeth during each treatment while still achieving the same whitening results.

Referring first to FIG. 1, a tooth whitening system 1000 is illustrated in accordance with an embodiment of the present invention. The tooth whitening system 1000 generally comprises a mouth tray 100 and a reservoir device 200.

The reservoir device 200 can be any device configured to hold an amount of a tooth whitening composition prior to it being dispensed into the mouth tray 100 or otherwise dispensed in such a manner so that it can be put into contact with a user's teeth for whitening. Thus, in the exemplified embodiment the reservoir device 200 is a squeezable tube-like device having a body portion 201 and a nozzle portion 202. A user can squeeze the body portion 201 of the reservoir device 200 to dispense the tooth whitening composition contained therein through the nozzle portion 202. However, the invention is not to be limited to the reservoir device 200 being a squeezable tube-like device. In other embodiments, the reservoir device 200 may be any container having an interior cavity that can hold the tooth whitening composition. For example, the reservoir device 200 could be a cylindrical, polygonal, or the like shaped container with a removable lid such that when the lid is removed a user can use a spoon, spatula, cotton swab, or other apparatus to remove some of the tooth whitening composition therefrom for application to the teeth (either directly or indirectly via the mouth tray 100 or similar device). In still other embodiments, the reservoir device 200 could be a tube-like device as shown in FIG. 1, but instead of being squeezable it may include an elevator-style dispensing mechanism therein. Thus, the tube-like device may be formed from a rigid material so that it is not squeezable, but it may include an actuator mechanism for activating the elevator-style dispensing mechanism. In still other embodiments, the tooth whitening composition may be provided on a strip and the strip can be attached or adhered to the mouth tray to "dispense" the tooth whitening composition onto the mouth tray. Thus, the strip may be considered the reservoir device. It should be appreciated that various permutations are possible for the reservoir device and the invention is not to be limited by the structure thereof shown in the accompanying drawings unless the same is specifically claimed.

In the exemplified embodiment, the mouth tray 100 generally comprises an intraoral mouthpiece (hereinafter "the mouthpiece") 110 and a handle 150. The mouthpiece 110 comprises a concave front surface 111 from which electromagnetic radiation, and more specifically light, is emitted onto the tooth whitening composition and/or the user's teeth during use and a convex rear surface 112. The handle 150 extends from the convex rear surface 112. Thus, the handle 150 extends from the mouthpiece 110 in a direction generally opposite the direction in which electromagnetic radiation/light is emitted from the mouthpiece 110. The handle 150 comprises a housing 151 that houses a control circuit 170 (see FIG. 4) of the mouth tray. During use, the mouthpiece 110 is inserted into the user's mouth/oral cavity and the housing 150 remains exterior to the user's mouth/oral cavity.

In the exemplified embodiment, the handle 150 comprises an actuator 152 (i.e., a power button) for activating the control circuit 170 for operation of the mouth tray 100. Specifically, actuation of the actuator 152 will power the mouth tray 100 on so that power is transmitted from a power source to an electromagnetic radiation source so that the electromagnetic radiation source can emit the electromagnetic radiation onto the user's teeth as described herein. The mouth tray 100 may power off automatically after a predetermined period of time, and/or the mouth tray 100 may power off upon a second actuation of the actuator 152. In the exemplified embodiment, the actuator 152 is a depressible button, but the invention is not to be so limited and other types of actuators may be used. Specifically, the actuator 152 can be any type of device that upon actuation powers on and/or off one or more of the electrical components stored within the housing 151. For example, the actuator 152 can be a slide switch, a touch pad, a knob, a capacitive sensor, or any other component that upon actuation causes the mouth tray 100 to function as described herein. The actuator 152 may be operably coupled to a processor so that upon depressing or otherwise actuating the actuator 152, the processor initiates operation of the mouth tray 100 (i.e., powers on the electromagnetic radiation or illumination source) as described in more detail below.

The mouthpiece 110 generally comprises a floor 113, an outer sidewall 114 extending from the floor 113, and an inner sidewall 115 extending from the floor 113. The inner and outer sidewalls 114, 115 are spaced apart from one another, thereby defining a channel 120 therebetween. In the exemplified embodiment, the inner and outer sidewalls 114, 115 both extend upwardly and downwardly from the floor 113 to thereby define an upper channel 120 for receiving a user's upper teeth and a lower channel (shown in FIGS. 1 and 4 but not labeled) for simultaneously receiving a user's lower teeth. However, the invention is not to be so limited in all embodiments and the inner and outer sidewalls 114, 115 may instead extend in only one direction from the floor 113 to define a singular channel (i.e., the channel 120) for receiving either the user's upper or lower teeth but not both simultaneously. The mouthpiece 110 is therefore a tray-shaped structure that is configured to receive either the user's upper teeth or the user's lower teeth, or both simultaneously. In some embodiments, the inner sidewall 115 may be omitted. Furthermore, the floor 113 may serve the purpose of acting as a bite guard such that the user can bite down on the floor 113 during use to hold the mouthpiece 110 in proper position within the oral cavity.

Figure 4:
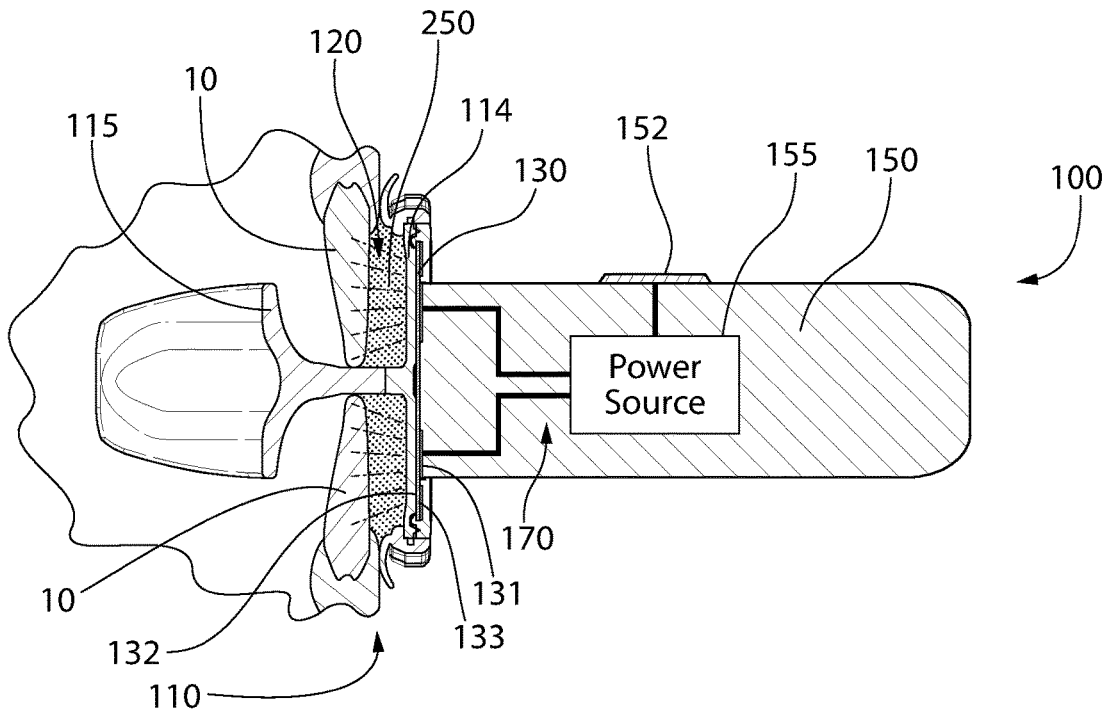
FIG. 4 is a schematic cross-sectional view illustrating the mouth tray at least partially inserted within an oral cavity of a user so that the user's teeth are in contact with the tooth whitening composition.

Referring to FIGS. 1 and 4 concurrently, the mouthpiece 110 comprises an electromagnetic radiation source (also referred to herein as an illumination source) 130 positioned along the outer sidewall 114. In the exemplified embodiment, the electromagnetic radiation source 130 is embedded within the outer sidewall 114 so that it is not exposed directly to the user's saliva when the mouthpiece 110 is positioned within the user's oral cavity. Thus, the electromagnetic radiation source 130 in the exemplified embodiment is not exposed along the concave front surface 111 of the mouthpiece 110. This may be done to protect the electromagnetic radiation source 130 against damage. However, the invention is not to be so limited in all embodiments and the electromagnetic radiation source 130 could be located on, exposed on, or form a part of the concave front surface 111 of the mouthpiece 110 in other embodiments.

The electromagnetic radiation source 130 may take on any of a number of different configurations. In the exemplified embodiment, the electromagnetic radiation source 130 comprises a lamp having a flexible sheet body 131 that can be bent to fit/match the contours of the outer sidewall 114 of the mouthpiece 110. The flexible sheet body 131 comprises a front surface 132 and a rear surface 133. A plurality of light emitters 134 may be embedded within or otherwise located on the flexible sheet body 131. The light emitters 134 may be printed onto the flexible sheet body 131 or attached to the flexible sheet body 131 in any other way desired. In one embodiment, the light emitted by the plurality of light emitters 134 has a wavelength in a range of 375 nm to 520 nm. In another embodiment, the light emitted by the plurality of light emitters 134 has a wavelength in a range of 400 nm to 430 nm. In a further embodiment, the light emitted by the plurality of light emitters 134 has a wavelength in a range of 400 nm to 420 nm, and in still another embodiment the wavelength is in a range of 405 nm to 415 nm. In one other embodiment, the wavelength is approximately 410 nm. The wavelength of light emitted by the light emitters 134 is generally known to be effective to whiten teeth.

The plurality of light emitters 134 are depicted schematically in FIG. 1. In FIG. 1, it appears as if the plurality of light emitters 134 are exposed on the front surface 111. However, as mentioned above, this is not necessary the case. Rather, the plurality of light emitters 134 may be embedded within the outer sidewall 114 yet the light emitted therefrom can pass through the outer sidewall 114. Thus, the location and positioning of the plurality of light emitters 134 in FIG. 1 is shown for ease of reference and understanding but is not intended to be limiting of the invention in all embodiments.

As noted above, the light emitters 134 may be printed onto the flexible sheet body 131. For example, printed LEDs may be formed by depositing micro LED chips via a conductive ink formulation that can be printed in any shape to best conform to the teeth and jaw structure, which is ideal for optimized efficacy. Specifically, gallium nitride may be used to form the LEDs in some embodiments, which may then be mixed with resin and binders to form an ink, and a standard screen printer may be used to deposit the resulting ink over a desired surface. The electrically conductive ink may include electrically conductive materials, such as by infusing graphite or other conductive materials into the ink.

Although described herein as being printed LEDs, the plurality of light emitters 134 may in certain embodiments be any type of light source, particularly solid state light sources, which may include LEDs, OLEDs, HBLEDs, electroluminescent elements, or the like. In certain other embodiments, the plurality of light emitters 134 can be printed inorganic LEDs, micro conventional LEDs that are surface mounted to a flexible substrate/circuit, organic LEDs (OLEDs), or electroluminescence. In still other embodiments, the plurality of light emitters 134 can be any of the LEDs noted herein mounted to a rigid rather than a flexible substrate. In other embodiments, however, the light emitted by the mouthpiece 110 may be generated with other light sources that are either embedded in the outer wall 114 and/or transmitted to the light emitting surface of the mouthpiece 110 using light piping or other suitable techniques. However, in certain preferred embodiments the mouth tray 100 comprises the electromagnetic radiation/illumination source 130.

Still referring to FIGS. 1 and 4, the mouth tray 100 also comprise a power source 155 located within the housing 150. The control circuit 170 may comprise the actuator 152, the power source 155, and the electromagnetic radiation source 130 in some embodiments. The control circuit 170 may also comprise a controller, memory device, or the like in some embodiments as mentioned briefly below. The power source 155 may comprise one or more batteries or any other device configured to supply power to the other electronic devices of the mouth tray 100.

The power source 155 is operably coupled to the electromagnetic radiation source 130 so that upon activation (such as by pressing the actuator button 152), power is supplied from the power source 155 to the electromagnetic radiation source 130. The mouth tray 100 may also comprise additional circuitry and electronic components, such as a processor or controller, that is operably coupled to the power source 155 and to the electromagnetic radiation source 130. The processor or controller may comprise a memory or be operably coupled to a memory device that stores processing instructions. For example, in some embodiments the electromagnetic radiation source 130 may be configured to be powered off after being powered on for a predetermined period of time (e.g. 10 minutes). Thus, the processor may store such instructions and may be configured to power the electromagnetic radiation source 130 off after expiration of the predetermined period of time.

Additional details of the mouth tray 100 which may, but is not required, to be used in accordance with the invention described herein, may be found in U.S. Pat. No. 10,369,375, filed on Dec. 22, 2015, the entirety of which is incorporated herein by reference. Of course, as has been noted herein, the invention, which is directed primarily to a method of whitening teeth, is not to be limited to the mouth tray 100 shown and described herein and any type of mouth tray that is commonly used for tooth whitening can be used whether the mouth tray includes an electromagnetic radiation source or electromagnetic radiation/light from an electromagnetic radiation/illumination source that is separate from the mouth tray 100 can be emitted onto compositions placed in the channels 120.

Figure 2:
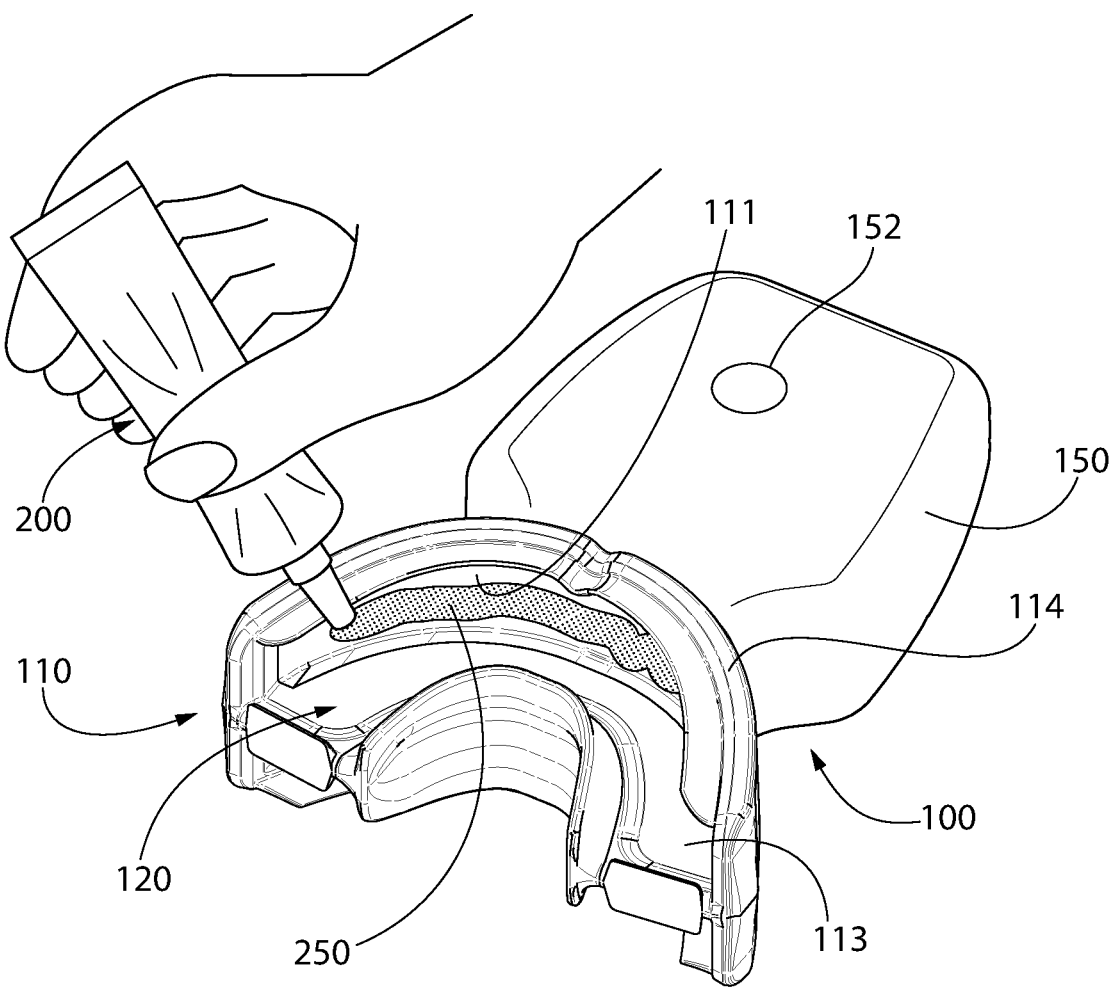
FIG. 2 is a perspective view illustrating the tooth whitening composition being dispensed from the reservoir device into a channel of the mouth tray.
Figure 3:
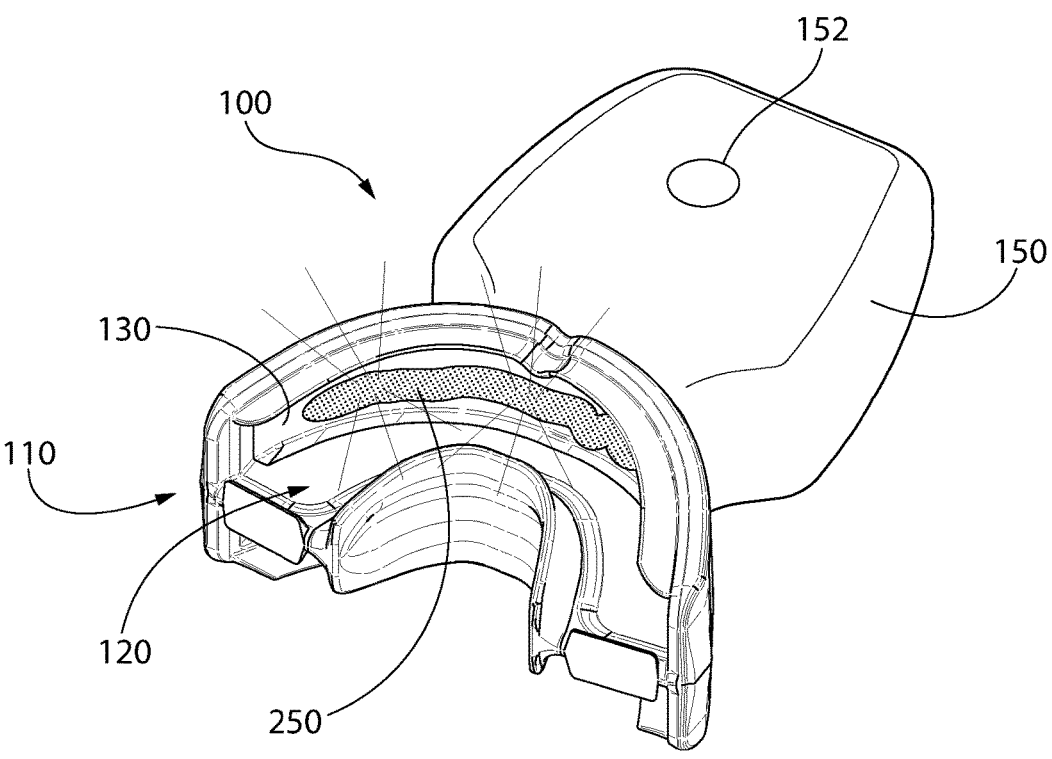
FIG. 3 is a perspective view illustrating the tooth whitening composition being pretreated with light prior to placement of the mouth tray in an oral cavity of a user.
Figure 5:
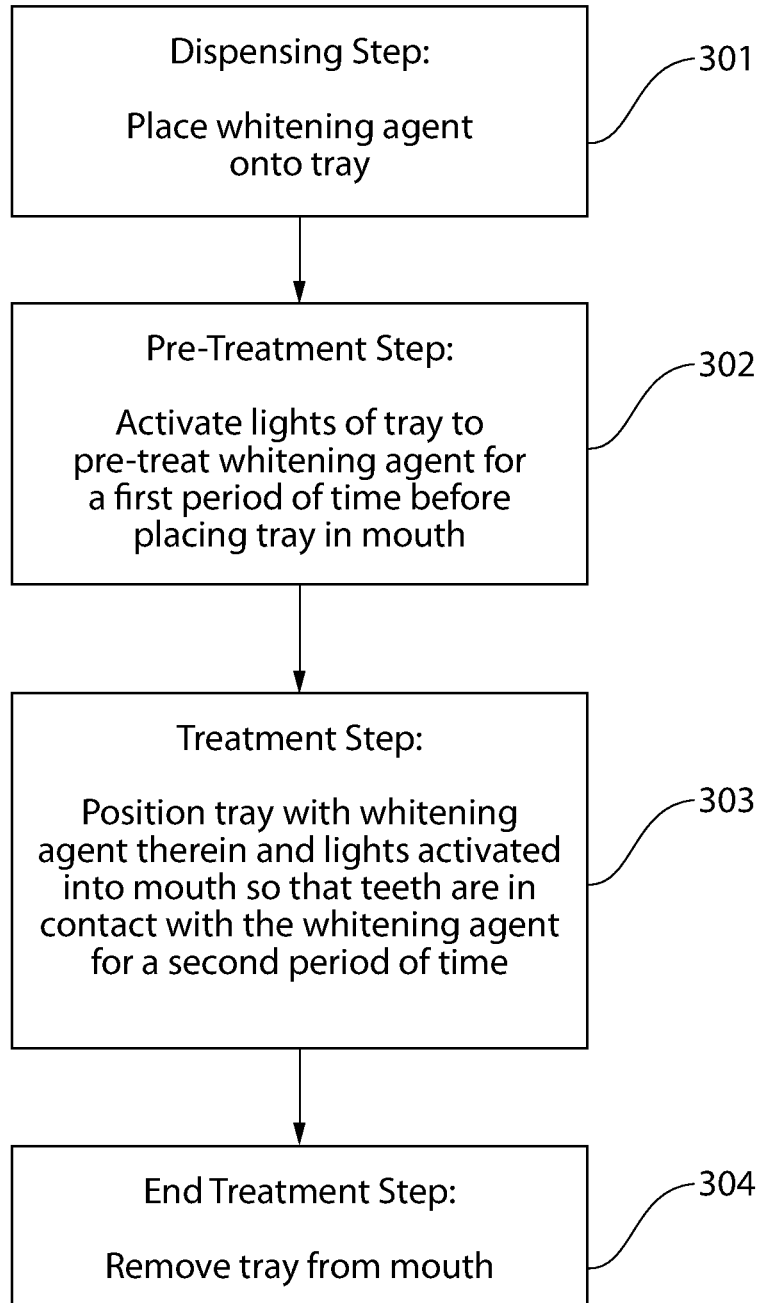
FIG. 5 is a flow chart describing the steps of the method of whitening teeth in accordance with an embodiment of the present invention.

Referring to FIGS. 2-4 sequentially in conjunction with FIG. 5, a method of whitening teeth in accordance with the exemplified embodiment will be described. Referring to FIGS. 2 and 5 concurrently, the first step in the tooth whitening method is the dispensing step 301. In the dispensing step 301, the tooth whitening composition 250 is dispensed from the reservoir device 200 into the channel 120 of the mouthpiece 110 of the mouth tray 100. In the exemplified embodiment, the tooth whitening composition 250 is being dispensed directly onto the concave front surface 111 of the mouthpiece 110, which is the front surface of the outer sidewall 114 from which the electromagnetic radiation/light is emitted. The reason for this is that because the electromagnetic radiation/light is emitted from the front surface 111 of the mouthpiece 110, by placing the tooth whitening composition 250 on that same surface it can be ensured that the electromagnetic radiation/light will be emitted onto the tooth whitening composition 250 for activation thereof. However, the invention is not to be limited to this and in other embodiments the tooth whitening composition 250 can be dispensed to any location on the mouth tray 100, and more particularly within the channel 120 of the mouthpiece 110 of the mouth tray 100. Thus, for example, the tooth whitening composition 250 could instead or additionally be dispensed onto the floor 113 of the channel 120. What is important is that the tooth whitening composition 250 is dispensed into the channel 120 (or otherwise onto the mouthpiece 110 of the mouth tray 100) at a location that will ensure that the tooth whitening composition 250 comes into contact with the user's teeth during tooth whitening. The tooth whitening composition 250 should also be positioned at a location that ensures that light or electromagnetic radiation emitted by the electromagnetic radiation source 130 is emitted onto the tooth whitening composition 250.

The tooth whitening composition 250 may be any composition known for use in whitening teeth. In one embodiment, the active ingredient in the tooth whitening composition 250 is hydrogen peroxide. In some embodiments, the tooth whitening composition 250 may comprise hydrogen peroxide in a concentration of greater than 0.1%. In other embodiments, the tooth whitening composition 250 may comprise hydrogen peroxide in a concentration that is greater than 1%, or in some embodiments between 1% and 9%. In still other embodiments, the tooth whitening composition 250 may comprise hydrogen peroxide in a concentration between 1% and 12%. In yet other embodiments, the tooth whitening composition 250 may comprise hydrogen peroxide in a concentration of approximately 9%. The term approximately as used herein includes concentrations that are within a range that is the percentage provided plus or minus the percentage provided multiplied by 0.05. Thus, for a concentration of 9%, 9*0.05 equals 0.45, so approximately 9% would include a range of 8.55% to 9.45%.

Referring to FIGS. 3 and 5 concurrently, the next step in the method is the pre-treatment step 302. In the pre-treatment step 302 in accordance with the exemplified embodiment, the user activates the actuator 152, which causes the electromagnetic radiation source or illumination source 130 to emit electromagnetic radiation/light onto the tooth whitening composition 250 located within the channel 120 of the mouthpiece 110 (or otherwise located on the mouth tray 100). The pre-treatment step 302 takes place before the mouthpiece 110 is inserted into the user's oral cavity/mouth. Thus, the electromagnetic radiation or light is emitted from the electromagnetic radiation/illumination source 130 onto the tooth whitening composition 250 before placing the teeth into contact with the tooth whitening composition 250. The pre-treatment step 302 may activate the tooth whitening composition 250 so that once the tooth whitening composition 250 comes into contact with the user's teeth, the whitening process is accelerated. By pretreating the tooth whitening composition 250 with electromagnetic radiation/light before placing the tooth whitening composition 250 into contact with the user's teeth, the amount of time that the tooth whitening composition 250 needs to be in contact with the teeth to achieve the desired amount of whitening can be reduced, as described further herein below.

In the exemplified embodiment, the mouth tray 100 comprises the electromagnetic radiation/illumination source 130. Thus, the user activates the actuator 152 on the mouth tray 100, which causes the electromagnetic radiation/illumination source 130 to emit electromagnetic radiation or light. However, the invention is not limited to requiring that the mouth tray 100 comprise the electromagnetic radiation source 130 in all embodiments. In some embodiments, a separate electromagnetic radiation or illumination source may be brought near the mouth tray 100, activated, and held in such a way so that the electromagnetic radiation or light emitted therefrom is emitted onto the tooth whitening composition 250 in the mouth tray 100 during this pretreatment step 302.

Regardless of the specific manner in which it is achieved, the pretreatment step 302 includes emitting light (or electromagnetic radiation) onto the tooth whitening composition 250 that is in the mouth tray 100 before placing the mouthpiece 110 of the mouth tray 100 into the oral cavity. This pretreatment step 302 takes place for a first period of time prior to inserting the mouth tray 100 (or the mouthpiece 110 thereof) into the user's oral cavity. In some embodiments, the first period of time may be referred to herein as a non-contact treatment time. Additional details about the first period of time will be provided below.

Referring to FIGS. 4 and 5, the next step in the method of whitening teeth is a treatment step 303. After expiration of the first period of time associated with the pretreatment step 302, the mouthpiece 110 of the mouth tray 100 is inserted into the user's oral cavity or mouth. Specifically, the mouth tray 110 is inserted into the user's oral cavity so that the user's teeth 10 are in contact with the tooth whitening composition 250 in the mouth tray 110. In the exemplified embodiment, this is achieved by placing the user's teeth in the channel 120 of the mouthpiece 110 of the mouth tray

100. However, the invention is not limited to the structure of the mouth tray 100 in all embodiments so other techniques for placing the user's teeth into contact with the tooth whitening composition 250 can be used in the treatment step 303. During the treatment step 303, the electromagnetic radiation/illumination source 230 remains powered on so that electromagnetic radiation/light continues to be emitted onto the tooth whitening composition 250 in the mouth tray 100. The mouth tray 100 is kept inside of the user's oral cavity in this way for a second period of time. In some embodiments, the second period of time may be referred to herein as a contact treatment time.

After expiration of the second period of time, the whitening treatment is complete and an end treatment step 304 takes place whereby the mouth tray 100 is removed from the user's oral cavity. In some embodiments as described herein, after expiration of the second period of time the mouth tray 100 will automatically power the electromagnetic radiation/illumination source 230 off (i.e., deactivate the electromagnetic radiation source). In other embodiments, the user may have to press the actuator 152 a second time to power the electromagnetic radiation/illumination source 230 off after expiration of the second period of time.

In the method described herein, a sum of the first period of time associated with the pretreatment step 302 and the second period of time associated with the treatment step 303 equals a total treatment time. Thus, as soon as the electromagnetic radiation source 230 is activated so that electromagnetic radiation (e.g., light) is emitted onto the tooth whitening composition 250, a timer associated with the total treatment time starts. In some embodiments, the first period of time is at least 20% of the total treatment time. In other embodiments, the first period of time is at least 30% of the total treatment time. In still other embodiments, the first period of time is at least 40% of the total treatment time. In yet other embodiments, the first period of time is at least 50% of the total treatment time. In further embodiments, the first period of time is between 40% and 60% of the total treatment time. Thus, if the total treatment time is ten minutes (which it is in one preferred embodiment), then the first period of time may be two minutes while the second period of time may be eight minutes, or the first period of time may be three minutes while the second period of time may be seven minutes, or the first period of time may be four minutes while the second period of time may be six minutes, or the first period of time may be five minutes while the second period of time may also be five minutes. In some embodiments, the first period of time is at least two minutes and in other embodiments the first period of time is at least four minutes.

In one preferred embodiment, the total treatment time is ten minutes and the first period of time is at least two minutes. In another preferred embodiment, the total treatment time is ten minutes and the first period of time is at least three minutes. In another preferred embodiment, the total treatment time is ten minutes and the first period of time is at least four minutes. In another preferred embodiment, the total treatment time is ten minutes and the first period of time is at least five minutes. In yet another preferred embodiment, the total treatment time is ten minutes and each of the first and second periods of time is approximately five minutes.

In other embodiments, the various lengths of the first and second periods of time may be a ratio without regard to a particular amount of time. For example, in one particular embodiment of the present invention, a ratio of the first period of time to the second period of time may be approximately 1:1. Thus, if the total treatment time is fifteen minutes, then the first and second periods of time are both approximately seven and a half minutes. If the total treatment time is ten minutes, than the first and second periods of time are both approximately five minutes. In other embodiments, a ratio of the first period of time to the second period of time may be in a range of 0.6:1 and 1.5:1. In still other embodiments, a ratio of the first period of time to the second period of time may be in a range of 0.8:1 and 1.2:1, and in yet other embodiments a ratio of the first period of time to the second period of time may be in a range of 0.9:1 and 1.1:1.

As can be appreciated, the only time that the tooth whitening composition is in contact with the teeth is the second period of time. In certain conventional/standard treatments, there is no pretreatment (i.e., light is not emitted onto the tooth whitening composition prior to the tooth whitening composition being placed into contact with the teeth) and once the tooth whitening composition is placed inside the tray, the tray is positioned in the user's oral cavity and the illumination source is activated. Thus, the tooth whitening composition is in contact with the user's teeth for the entirety of the treatment time during which the light is activated. In such conventional/standard treatments, the tray often remains in the oral cavity with the tooth whitening composition in contact with the user's teeth for approximately ten minutes. In accordance with the method described herein, the pretreatment and treatment steps 302, 303 combined may last for approximately ten minutes. Thus, using the inventive method that includes the pretreatment step 302, the contact time between the tooth whitening composition and the teeth can be reduced as compared with a conventional or standard treatment.

In some aspects, the invention may be directed to an oral treatment apparatus, such as the mouth tray 100, that is configured to perform the method noted above. Such an oral treatment apparatus may comprise a timer device, a first indicator, a second indicator, and a processor that are operably coupled together. The timer device and the processor may be located within the handle 150 in some embodiments. The first and second indicators may be located in the handle 150 or in the mouthpiece. The processor configured to start the timer device upon activation of the electromagnetic radiation source, activate the first indicator upon expiration of the first period of time to instruct the user to insert the mouth tray into the oral cavity; and activate the second indicator upon expiration of the second period of time to instruct the user to remove the mouth tray from the oral cavity.

The first and second indicators may be lights, sounds, vibrations, or the like. For example, the first indicator may be a first colored light and the second indicator may be a second colored light that is different than the fist colored light. Alternatively, the first indicator may be a light that blinks once and the second indicator may be a light that blinks twice. The first indicator may be a light and the second indicator may be a sound or a vibration, or vice versa. Thus, various permutations are possible within the scope of the invention described herein.

Figures 6A, 6B:
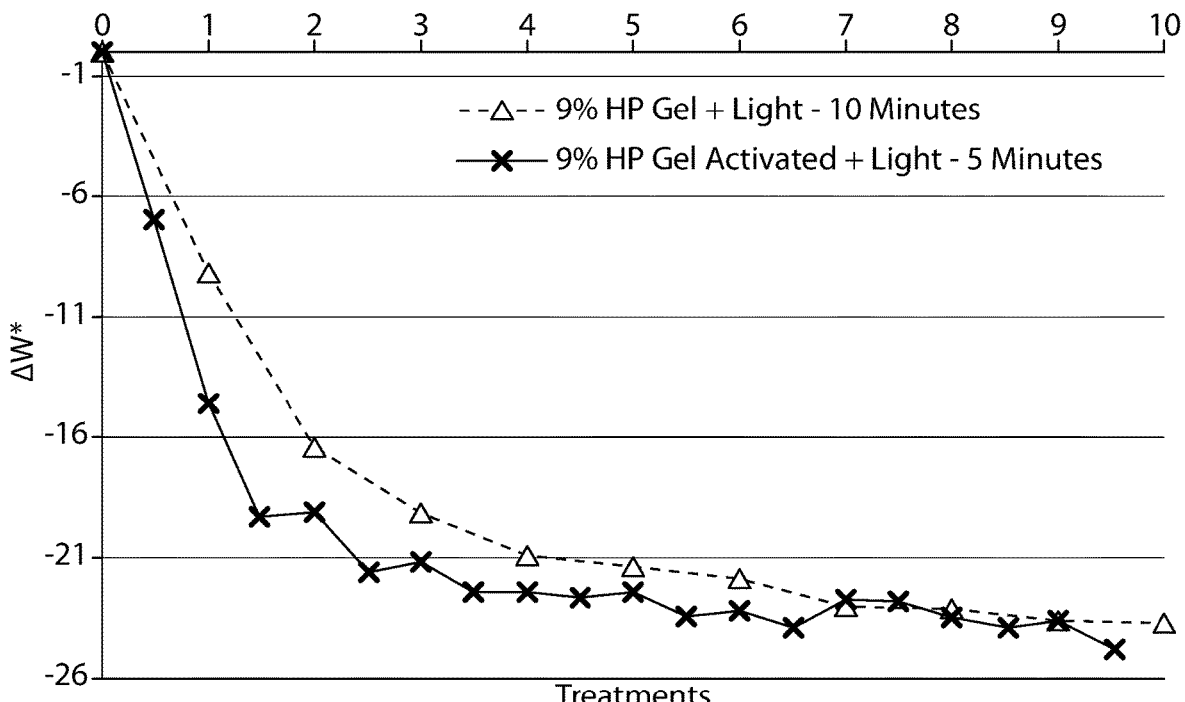
FIG. 6A is a table with first experimental data.
FIG. 6B is a graphical representation of the first experimental data.

Some experiments were performed to test the whitening effect utilizing the methods described herein as compared with the standard/conventional methods that omit a pretreatment step as described herein. The first experiment was done using a tooth whitening composition having a hydrogen peroxide concentration of 9% and the results of the first experiment are shown in the table of FIG. 6A and the graph of FIG. 6B. The test results showed that with 9% hydrogen peroxide tooth whitening composition, using the pretreatment step resulted in the same or better whitening despite having half of the contact time with the tooth surface as compared with standard/conventional methods that do not include the pretreatment step. Although after a single treatment (Treatment #1) the results were better without the pretreatment, every other treatment showed either very similar or better results using the pretreatment step as compared to not using the pretreatment step. The experimental results show that achieving similar or better whitening results with less contact time between the teeth and the tooth whitening composition can be achieved with the method described herein.

In the experiment, in-vitro whitening efficacy of the tooth whitening composition comprising hydrogen peroxide at a concentration of 9% was tested via bleaching studies within the mouth tray 100. The details of the in-vitro testing procedure and results are described below and shown in FIGS. 6A and 6B.

Artificially stained bovine enamel samples were brushed with 1:1 silica toothpaste to artificial saliva slurry for fifteen minutes. The teeth were rinsed thoroughly and CieLab measurements (L*a*b) were recorded with a handheld spectrophotometer. The CieLab measurements express color as three values: L* for the lightness from black (0) to white (100), a* from green (−) to red (+), and b* from blue (−) to yellow (+). CieLab was designed so that the same amount of numerical change in these values corresponds to roughly the same amount of visually perceived change. Bovine enamel with L values between 58 and 64 were used for the study.

Six bovine enamel samples were assigned to each test group. Their baseline L*a*b values were recorded and balanced between groups to ensure statistical equivalence.

Two different testing methods were compared. Using the first method, a tooth whitening composition (i.e., whitening gel) was dispensed into the mouth tray 100, bovine enamel samples (i.e., teeth) were placed in the tray in contact with the tooth whitening composition, and then the unit was turned on so that light was emitted from the illumination source of the mouth tray 100. The teeth were placed as closely to the illumination source (e.g., LEDs) as possible. The teeth were kept in contact with the tooth whitening composition and the light was kept on for a treatment time of ten minutes. At the end of the treatment time (which was ten minutes for this first testing method, with the teeth being in contact with the tooth whitening composition and the light being activated for the entirety of the ten minutes), the bovine samples were removed from the tray and rinsed thoroughly to remove all of the tooth whitening composition from the surface of the enamel. L*a*b measurements were recorded. The process was repeated ten times. This first method is the conventional/standard method because it does not include a pretreatment step. The results of this first method are shown in the first row of the table in FIG. 6A and depicted in the graph as the line with triangles.

Using the second method, the same tooth whitening composition (9% hydrogen peroxide concentration) was dispensed into the mouth tray 100 and the LEDs were turned on before placing the bovine enamel samples (i.e., teeth) into contact with the tooth whitening composition (i.e., the pretreatment step 302). After five minutes had elapsed with the light being emitted onto the tooth whitening composition in the mouth tray 100, bovine enamel samples were placed in the mouth tray 100 in contact with the tooth whitening composition and positioned as closely to the illumination source (e.g., LEDs) as possible. After five additional minutes had elapsed with the bovine enamel samples in contact with the tooth whitening composition and the illumination source powered on, the bovine samples were removed from the tray and rinsed thoroughly to remove all of the tooth whitening composition from the surface of the enamel. L*a*b measurements were recorded. The process was repeated ten times. This second method is the method of the present invention described herein and shown, for example, in FIG. 5 because it includes the pretreatment step 302. The results of this second method are shown in the second row of the table in FIG. 6A and depicted in the graph as the line with X's. Both the first method and the second method involve a ten minute total treatment time. In the first method the teeth are in contact with the tooth whitening composition for the entire ten minute treatment and in the second method the teeth are in contact with the tooth whitening composition for five of the ten minutes.

The recorded L*a*b values were used to calculate a whitening index W*. W* incorporates the L, a, and b values to describe how close the measured color is to true white. It is calculated according to the following equation.

$$W^* = (a2 + b2 + (L^* - 100)2)1/2$$

The data in the table provided as FIG. 6A and the graph provided as FIG. 6B is reporting the change in W* value after treatment (ΔW*). Larger ΔW*=whiter color.

Surprisingly, the pretreatment step of the second method that included exposing the tooth whitening composition to 410 nm light before placing the teeth into contact with the tooth whitening composition resulted in a similar whitening benefit delivered or an increase in whitening benefit delivered as compared with the first method that did not include the pretreatment step. This was unexpected due to the reduction of contact time of tooth whitening composition with the tooth from ten minutes to five minutes. This reduction limits the theoretical amount of peroxide that can penetrate the surface of the tooth. Thus, there was an expectation that the whitening benefit delivered would be reduced, but that was not the case. Thus, it has been determined that the pretreatment step allows for a reduction in contact time between the tooth whitening composition and the tooth while achieving a similar if not better whitening result.

Figures 7A, 7B:
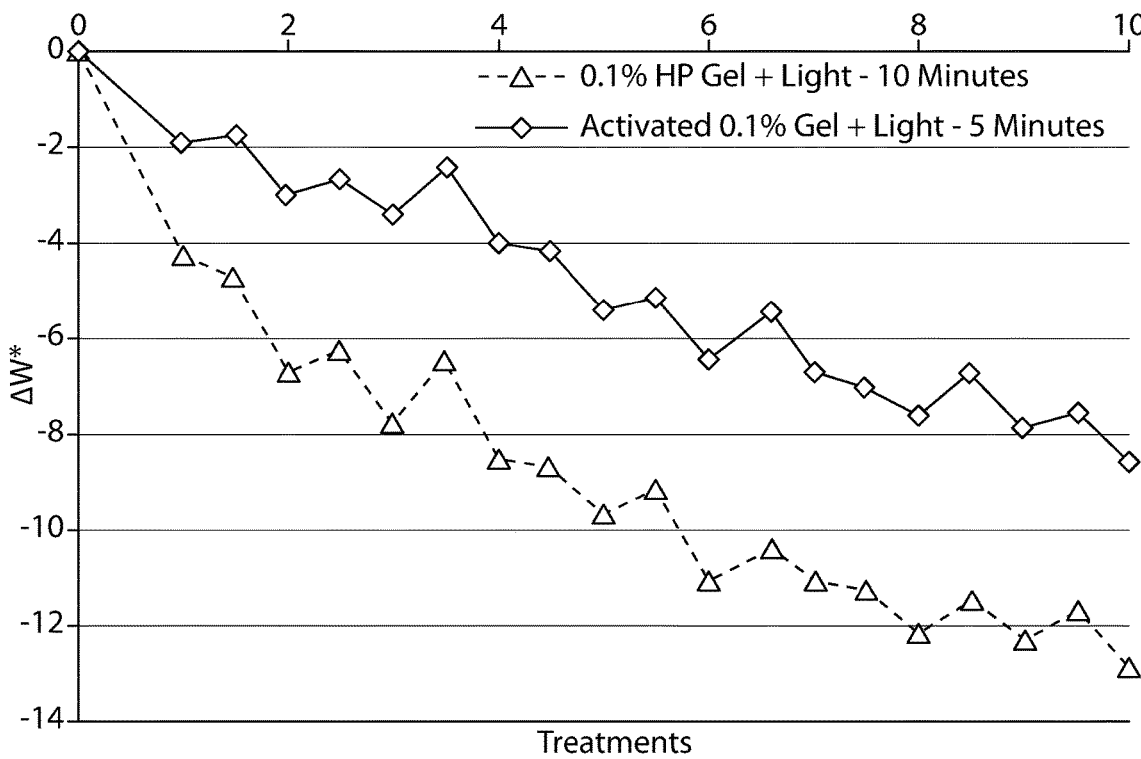
FIG. 7A is a table with second experimental data.
FIG. 7B is a graphical representation of the second experimental data.

Referring now to FIGS. 7A and 7B, the same experiment mentioned above was repeated with the only difference being that the tooth whitening composition contained hydrogen peroxide having a concentration of 0.1% In this second experiment, when the tooth whitening composition was "activated" with the pretreatment step described herein and then applied to the teeth with a reduced period of time (five minutes instead of ten minutes), the whitening benefit was reduced. Thus, the same benefits of being able to reduce contact time between the tooth whitening composition and the teeth while maintaining similar or better whitening benefits was not achieved with the 0.1% hydrogen peroxide tooth whitening composition.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A method of whitening teeth comprising:
dispensing a tooth whitening composition from a reservoir device into a channel of a mouth tray;
prior to placing the mouth tray into an oral cavity of a user, activating an electromagnetic radiation source to emit electromagnetic radiation onto the tooth whitening composition in the channel of the mouth tray for a first period of time to pretreat the tooth whitening composition;
after expiration of the first period of time, inserting the mouth tray into the oral cavity of the user so that the user's teeth are in contact with the tooth whitening composition in the channel for a second period of time to achieve a desired whitening effect; and
after expiration of the second period of time, removing the mouth tray from the oral cavity of the user and deactivating the electromagnetic radiation source;
wherein a sum of the first period of time and the second period of time equals a total treatment time, wherein the first period of time is at least 20% of the total treatment time, and wherein the first period of time initiates a chemical change in the tooth-whitening composition prior to contact of the tooth-whitening composition with the user's teeth, thereby reducing the second period of time required to achieve the desired whitening effect.

2. The method according to claim 1 wherein the first period of time is between 40% and 60% of the total treatment time.

3. The method according to claim 1 wherein the total treatment time is ten minutes.

4. The method according to claim 1 wherein the first period of time is at least two minutes.

5. The method according to claim 1 wherein the mouth tray comprises the electromagnetic radiation source, wherein the mouth tray comprises a floor, an inner sidewall, and an outer sidewall that collectively define the channel, and wherein the electromagnetic radiation source comprises a plurality of lighting elements located along the outer sidewall of the mouth tray.

6. The method according to claim 1 wherein the tooth whitening composition comprises hydrogen peroxide.

7. The method according to claim 6 wherein a concentration of the hydrogen peroxide in the tooth whitening composition is approximately 9%.

8. The method according to claim 1 wherein the light emitted from the electromagnetic radiation source has a wavelength between 400 nm and 420 nm.

9. An oral treatment apparatus configured to perform the method according to claim 1, wherein the oral treatment apparatus comprises:
a timer device;
a first indicator;
a second indicator; and
a processor configured to:
start the timer device upon activation of the electromagnetic radiation source;
activate the first indicator upon expiration of the first period of time to instruct the user to insert the mouth tray into the oral cavity; and activate the second indicator upon expiration of the second period of time to instruct the user to remove the mouth tray from the oral cavity.

10. A method of whitening teeth comprising:
dispensing a tooth whitening composition onto a mouth tray;
emitting light onto the tooth whitening composition on the mouth tray for a first period of time;
after expiration of the first period of time, inserting the mouth tray into an oral cavity of a user so that the user's teeth are in contact with the tooth whitening composition on the mouth tray for a second period of time to achieve a desired whitening effect; and
wherein a sum of the first and second periods of time equals a total treatment time, and wherein the first period of time is at least 20% of the total treatment time; and
wherein the first period of time initiates a chemical change in the tooth-whitening composition prior to contact of the tooth-whitening composition with the user's teeth, and wherein the second period of time required to achieve the desired whitening effect is reduced as a result of the initiated chemical change.

11. The method according to claim 10 wherein the first period of time is at least 30% of the total treatment time.

12. The method according to claim 11 wherein the first period of time is at least 40% of the total treatment time.

13. The method according to claim 10 wherein the tooth whitening composition comprises hydrogen peroxide having a concentration greater than 1%.

14. The method according to claim 13 wherein the tooth whitening composition comprises hydrogen peroxide having a concentration of approximately 9%.

15. The method according to claim 10 wherein the light is emitted onto the tooth whitening composition on the mouth tray during the second period of time while the teeth are in contact with the tooth whitening composition on the mouth tray.

16. The method according to claim 10 wherein the light is emitted onto the tooth whitening composition on the mouth tray for an entirety of the total treatment time.

17. The method according to claim 10 wherein the mouth tray comprises an illumination source, and wherein the illumination source is configured to emit the light onto the tooth whitening composition on the mouth tray, and wherein the light emitted from the illumination source has a wavelength between 400 nm and 420 nm.

18. The method according to claim 10 wherein the teeth are not in contact with the tooth whitening composition during the first period of time.

19. A method of whitening teeth comprising:
dispensing a tooth whitening composition onto a mouth tray;
emitting light onto the tooth whitening composition on the mouth tray for a non-contact treatment time; and
inserting the mouth tray into an oral cavity of a user so that the user's teeth are in contact with the tooth whitening composition on the mouth tray for a contact treatment time to achieve a desired whitening effect;
wherein a ratio of the non-contact treatment time to the contact treatment time is approximately 1:1; and
wherein the non-contact treatment time initiates a chemical change in the tooth-whitening composition prior to contact of the tooth whitening composition with the user's teeth, thereby reducing the contact time required to achieve the desired whitening effect by at least 20% relative to a whitening method of equal total duration in which the non-contact treatment time is omitted.

20. The method of whitening teeth according to claim 19 wherein a sum of the non-contact treatment time and the contact treatment time is a total treatment time, and the total treatment time is ten minutes.

* * * * *